US010066001B2

(12) United States Patent
Dowd et al.

(10) Patent No.: US 10,066,001 B2
(45) Date of Patent: Sep. 4, 2018

(54) ENHANCED LIQUID FORMULATION STABILITY OF ERYTHROPOIETIN ALPHA THROUGH PURIFICATION PROCESSING

(71) Applicant: Apotex Inc., Toronto (CA)

(72) Inventors: Jason Everett Dowd, Brampton (CA); Robert Weik, Hohe Wand-Stollhof (AT); Thomas Hemetsberger, Klosterneuburg (AT)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 14/775,248

(22) PCT Filed: Mar. 14, 2014

(86) PCT No.: PCT/CA2014/000252
§ 371 (c)(1),
(2) Date: Sep. 11, 2015

(87) PCT Pub. No.: WO2014/138921
PCT Pub. Date: Sep. 18, 2014

(65) Prior Publication Data
US 2016/0024165 A1 Jan. 28, 2016

Related U.S. Application Data

(60) Provisional application No. 61/792,991, filed on Mar. 15, 2013.

(51) Int. Cl.
C07K 1/18 (2006.01)
C07K 1/20 (2006.01)
C07K 1/22 (2006.01)
C12N 5/00 (2006.01)
C12N 15/09 (2006.01)
C07K 14/505 (2006.01)
C07K 14/50 (2006.01)
A61K 38/18 (2006.01)

(52) U.S. Cl.
CPC .............. C07K 14/505 (2013.01); C07K 1/18 (2013.01); C07K 1/20 (2013.01); C07K 14/50 (2013.01); C12N 5/00 (2013.01); C12N 15/09 (2013.01); A61K 38/1816 (2013.01)

(58) Field of Classification Search
None
See application file for complete search history.

(56) References Cited

U.S. PATENT DOCUMENTS

| 4,677,195 A | 6/1987 | Hewick |
| 4,703,008 A | 10/1987 | Lin |
| 5,547,922 A | 8/1996 | Ma |
| 5,641,670 A | 6/1997 | Treco et al. |
| 5,688,679 A | 11/1997 | Powell |
| 5,733,761 A | 3/1998 | Treco et al. |
| 5,756,349 A | 5/1998 | Lin |

| 2006/0099674 A1* | 5/2006 | Alliger ............... C07K 14/505 435/69.1 |
| 2012/0264688 A1* | 10/2012 | Hinderer ............. C07K 14/505 514/7.7 |
| 2013/0157293 A1* | 6/2013 | Branum .................. C12N 9/93 435/7.92 |

FOREIGN PATENT DOCUMENTS

| EP | 1394179 A1 | 3/2004 |
| EP | 1428878 A1 | 6/2004 |
| EP | 1127104 B1 | 11/2008 |
| WO | 1990011354 A1 | 10/1990 |
| WO | 1991006667 A1 | 5/1991 |
| WO | 1993009222 A2 | 5/1993 |
| WO | 1994012650 A2 | 6/1994 |
| WO | 1995031560 A1 | 11/1995 |
| WO | 2001035914 A1 | 5/2001 |
| WO | 2003045996 A1 | 6/2003 |
| WO | 2003046187 A1 | 6/2003 |
| WO | 2011035914 A1 | 3/2011 |

OTHER PUBLICATIONS

US 5,733,746, 03/1998, Treco et al. (withdrawn)
Li et al. Refolding of superoxide dismutase by ion-exchange chromatography. Biotechnology Letters vol. 24:919-923 (2002).*
Miyake, T., et al., "Purification of Human Erythropoietin", Journal of Biological Chemistry, American Society for Biochemistry and Molecular Biology, vol. 252, No. 15, pp. 5553-5564, 1997.
Supplementary European Search Report dated Jul. 19, 2016 in corresponding European Patent Application No. 14763151.9.
Egrie, J.C., et al., "Characterization and Biological Effects of Recombinant Human Erythropoietin", Immunobiology, vol. 172, Issues 3-5, pp. 213-224, 1986.
Erslev, A.J., "Humoral regulation of red cell production", Blood, vol. 8, No. 4, pp. 349-357, 1953.
Eschbach, J.W., et al., "Correction of the anemia of end-stage renal disease with recombinant human erythropoietin: Result of the Phase I and II clinical trial", New England Journal of Medicine, vol. 316, No. 2, pp. 73-78, 1987.
Eschbach, J.W., et al., "Recombinant Human Erythropoietin in Anemic Patients with End-Stage Renal Disease: Results of a Phase III Multicenter Clinical Trial", Annals of Internal Medicine, vol. 111, No. 12, pp. 992-1000, 1989.
Hu, Y., et al., "An improved, inexpensive procedure for the large-scale purification of recombinant human erythropoietin", Biotechnol. Appl. Biochem., vol. 40, pp. 89-94, 2004.
International Search Report issued in International Application No. PCT/CA2014/000252, filed Mar. 14, 2014, dated Jun. 16, 2014.

(Continued)

Primary Examiner — Elizabeth Kemmerer
Assistant Examiner — Regina M DeBerry
(74) Attorney, Agent, or Firm — Cozen O'Connor

(57) ABSTRACT

A method for purifying rHuEPO through the use of a multi-step filtration process which provides for a rHuEPO product having superior stability and shelf-life.

11 Claims, 3 Drawing Sheets

(56) References Cited

OTHER PUBLICATIONS

Nimitz, et al., Structures of sialylated oligosaccharides of human erythropoietin expressed in recombinant BHK-21 cells, Eur. J. Biochem., vol. 213, Issue 1, pp. 39-56, 1993.
Reismann, K.R., M.D., "Studies of the Mechanism of Erythropoietic Stimulation in Parabiotic Rats during Hypoxia", Blood, vol. 5, pp. 372-380, 1950.
Sasaki, H., et al., "Carbohydrate Structure of Erythropoietin Expressed in Chinese Hamster Ovary Cells by a Human Erythropoietin cDNA", The Journal of Biological Chemistry, vol. 262, No. 25, pp. 12059-12076, 1987.
Takeuchi, M., et al., "Comparative Study of the Asparagine-linked Sugar Chains of Human Erythropoietins Purified from Urine and the Culture Medium of Recombinant Chinese Hamster Ovary Cells", The Journal of Biological Chemistry, vol. 263, No. 8, pp. 3657-3663, 1988.

\* cited by examiner

ENHANCED LIQUID FORMULATION STABILITY OF ERYTHROPOIETIN ALPHA THROUGH PURIFICATION PROCESSING

FIELD OF INVENTION

The present application is generally related to methods and products resulting from said methods resulting in a highly stable erythropoietin alpha product having a substantially increased shelf life over current erythropoietin alpha products.

BACKGROUND OF THE INVENTION

Erythropoietin (EPO) is a glycoprotein that stimulates erythroblast differentiation in bone marrow, thereby stimulating production of erythrocytes and increasing the circulation blood erythrocyte count. Human erythrocytes have a mean life of about 120 days, and therefore EPO is utilized to maintain the blood erythrocyte concentration to maintain an adequate level of red blood cells.

EPO's existence was first conceived in the early 1900's, but not definitively proven until sometime in the early 1950's through the work of Reissman and Erslev. See Carnot, et al., *C.R. Acad. Sci.* (*France*), 143:384-386 (1906); Carnot, et al., *C.R. Acad. Sci.* (*France*), 143:432-435 (1906); Reismann, *Blood* 5:372-380 (1950); and Erslev, *Blood* 8:349-358 (1953). It was determined that endogenous production of EPO is normally regulated by the level of tissue oxygenation. In general, hypoxia and anemia generally increase the production of EPO, which stimulates erythropoiesis. Normal plasma EPO levels range from 0.01 to 0.03 Units/mL and may see increases of 100 to 1000 fold during hypoxia or anemia events.

EPO functions by binding to and activating receptors on the surface of hematopoietic progenitor cells in the bone marrow. These cells serve to produce red blood cells and their activity rate is regulated through several hormones, including EPO. EPO serves to not only facilitate the production of red blood cells, but also serves as an anti-apoptotic chemical that modulates apoptosis in the progenitor cells.

When a body fails to produce sufficient red blood cells due to any number of reasons, the person is said to be anemic. Patients with chronic renal failure have impaired EPO production and this EPO deficiency is their primary cause of anemia. This failure is typically progressive and irreversible, requiring treatment with dialysis and/or other medications. A major breakthrough for these patients was the discovery of EPO and treatment with EPO.

EPO has excellent efficacy in the treatment of anemia and anemia derived from renal failure. See Eschbach, et al., *N. England J. of Med.* 316:73-38 (1987). However, while proven useful, the inability to produce EPO in significant quantities made its use severely limited. In the 1990's and 2000's the use of recombinant technology made it possible for obtain large amounts of proteins. U.S. Pat. No. 5,688,679 (to Powell), U.S. Pat. No. 5,547,922 (to Lin), U.S. Pat. No. 5,756,349 (to Lin), U.S. Pat. No. 4,703,008 (to Lin), and U.S. Pat. No. 4,677,195 (to Hewick et al.) provide guidance to manufacture of large scale production of recombinant EPO, each of which are incorporated by reference herein, in their entirety.

Recombinant human EPO (rHuEPO), or Erythropoietin Alfa, is a 165 amino acid glycoprotein manufactured by recombinant DNA. Egrie J C, et al., *Immunobiol* 1986; 72:213-224. Typically, the manufacture of rHuEPO is obtained by expression vector that comprises a gene coding for human EPO in CHO-, BHK-, or HeLa cell lines, by recombinant DNA technology or by endogenous gene activation. For example in any of the following patents: U.S. Pat. Nos. 5,733,761, 5,641,670, and 5,733,746, and international patent publication Nos. WO 93/09222, WO 94/12650, WO 95/31560, WO 90/11354, WO 91/06667 and WO 91/09955, and EP 1127104.

RHuEPO entered the market in 1989 when the FDA first approved its use for the treatment of anemia from chronic renal failure. As with other recombinant glycoproteins, the use of rHuEPO and its bioavailability is influenced by the glycosylation pattern of the recombinant glycoprotein. Two models, Chinese hamster ovary and baby hamster kidney (CHO and BHK-21) host cells have been thoroughly studied for their production of glycoforms that most closely resemble the natural human EPO forms. See Sasaki et al., *J. Biol. Chem* 1987; 262:12059-12076; Takeuchi et al., *J. Biol. Chem* 1988; 263:3657-3663; Nimitz et al., *Eur. J. Biochem.* 1993 213:39-56.

EPO and rHuEPO can be utilized to treat a number of patients, for example, those suffering from chronic renal failure, where rHuEPO has been shown to stimulate erythropoiesis in anemic patients with chronic renal failure. Eschbach J W, et al., *NEJM* 1998; 316:73-78, Eschbach J W, et al., *Ann Intern. Med.* 1989; 111:992-1000. Other uses for rHuEPO include treatment for HIV infected patients using Zidovudine, cancer patients on chemotherapy, for treatment of anemic patients scheduled for elective surgery, as well as adult and pediatric patients on dialysis.

While rHuEPO is able to be produced in large quantities, sufficient to provide for its use in medicinal settings world wide, it requires strict storage conditions of between 2 to 8° C. and has a shelf life of 2 years. Enhanced short-term stability dosage forms are also available, through an added preservative of benzyl alcohol, which is meant to control microbiological degradation. This short shelf-life is due to the fact that the production of the rHuEPO exhibits heterogeneity (such as aggregates, dimers and monomers) and impurities due to the manufacturing process. These aggregates, dimers, monomers and other residual impurities from the manufacturing process serve as catalysts in any number of reactions that promote the formation of dimers, aggregates or other sub- and/or non-potent forms. If the temperature is raised above the 2 to 8° C. range, these sub- and/or non-potent forms become apparent in liquid stability studies. The commercial EPO products also indicate that freezing the product is not an option (results in aggregation—loss of potency and potential rise in immunogenic response). The key is to extend the 2 to 8° C. stability timeframe. While isoforms are particularly relevant clinically, from a stability perspective, the lack of impurities, especially those that would tend to catalyze reactions leading to sub- and/or non-potent forms are particularly relevant here. Also relevant is the choice of buffer components and their interaction with the primary packaging—in this case, the vial and stopper.

Methods of isolation and purification of EPO are known in the art and include methods using anion and cation exchange, reverse phase HPLC, hydroxyapatite, hydrophobic interaction, affinity exclusion, size exclusion, as well as other filtration and purification techniques. See WO 2001035914, which is incorporated by reference in its entirety herein.

Each of the known purification processes have limitations in removal of certain impurities. Accordingly, there is a need to create new methods of purification of rHuEPO to facilitate a rHuEPO product having significantly reduced impurities, thereby allowing for enhanced stability and thereby greater shelf life for manufactured products.

SUMMARY OF THE INVENTION

The present invention provides in its broadest aspect a method for purifying recombinant human erythropoietin alpha comprising: Subjecting unpurified erythropoietin alpha to anion exchange chromatography and collecting the resultant eluent, further subjecting the resultant eluent from step a to an ammonium sulfate precipitation step, further subjecting the resultant eluent from step b to a hydrophobic interaction chromatography step, further subjecting the resultant eluent from step c to a reversed phase chromatography step, further subjecting the resultant eluent from step d to a second anion exchange chromatography step, further subjecting the resultant eluent from step e to a gel filtration for buffer exchange, and further subjecting the resultant eluent from step f to nanofiltration for virus removal.

A further embodiment of the present disclosures is a method for purifying recombinant human erythropoietin alpha comprising: subjecting unpurified erythropoietin alpha to anion exchange chromatography and collecting the resultant eluent, and further subjecting the resultant eluent from step a to an ammonium sulfate precipitation step, and further subjecting the resultant eluent from step b to a hydrophobic interaction chromatography step, and further subjecting the resultant eluent from step c to a reversed phase chromatography step, and further subjecting the resultant eluent from step d to a second anion exchange chromatography step, and further subjecting the resultant eluent from step e to a gel filtration for buffer exchange, and further subjecting the resultant eluent from step f to nanofiltration for virus removal.

A further embodiment is directed to a recombinant human erythropoietin alpha product having a shelf life of at least four years manufactured by the following process wherein the process comprises the following steps: manufacturing a recombinant human erythropoietin alpha product and collecting the supernatant, clarifying the supernatant and subjecting the supernatant to a multi-step purification process comprising the following procedures in order: ultradiafiltration, anion exchange chromatography, ammonium sulfate precipitation, hydrophobic interaction chromatography, reversed phase chromatography, a second anion exchange chromatography step, gelfiltration, and nano filtration for virus removal; and producing a recombinant human erythropoietin alpha product that is substantially free of non-O-glycosylated recombinant human erythropoietin alpha isoforms.

A further embodiment is directed to a multi-step process for the production of a stable recombinant human erythropoietin alpha product that is substantially free of non-O-glycosylated recombinant human erythropoietin alpha isoforms comprising the following steps: subjecting a sample comprising recombinant human erythropoietin alpha and impurities to anion exchange chromatography and collecting the elute from said chromatography step, and further subjecting the resultant eluent from step a to an ammonium sulfate precipitation step, and further subjecting the resultant eluent from step b to a hydrophobic interaction chromatography step, and further subjecting the resultant eluent from step c to a reversed phase chromatography step, and further subjecting the resultant eluent from step d to a second anion exchange chromatography step, and further subjecting the resultant eluent from step 3 to a gel filtration for buffer exchange, and further subjecting the resultant eluent from step f to nanofiltration for virus removal.

A further embodiment is directed to a multi-step process for the production of a stable recombinant human erythropoietin alpha product that is substantially free of non-O-glycosylated recombinant human erythropoietin alpha isoforms comprising the following steps: subjecting a sample comprising recombinant human erythropoietin alpha and impurities to anion exchange chromatography wherein the buffers utilizes a low urea concentration, and collecting the elute from said chromatography step, and further subjecting the resultant eluent from step a to an ammonium sulfate precipitation step, and further subjecting the resultant eluent from step b to a hydrophobic interaction chromatography step, and further subjecting the resultant eluent from step c to a reversed phase chromatography step, and further subjecting the resultant eluent from step d to a second anion exchange chromatography step, and further subjecting the resultant eluent from step 3 to a gel filtration for buffer exchange, and further subjecting the resultant eluent from step f to nanofiltration for virus removal.

DETAILED DESCRIPTION OF THE PREFERRED EMBODIMENTS

Figure 1:
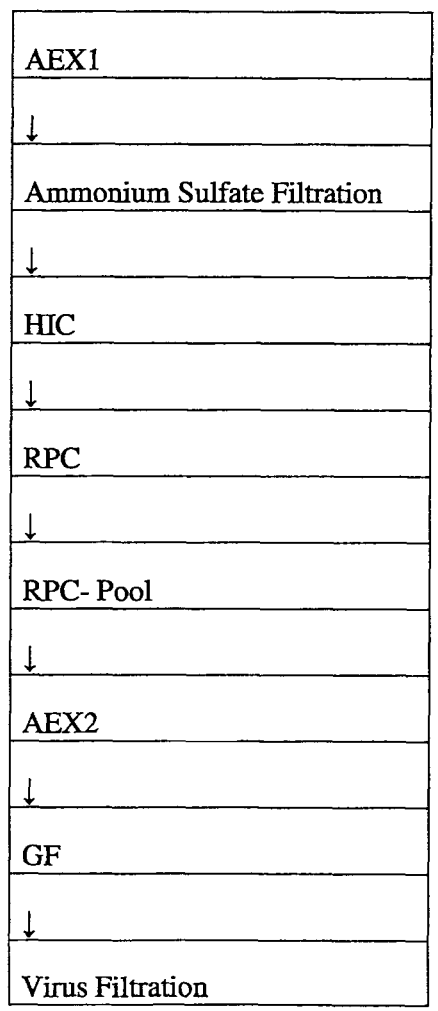
FIG. 1 is a flow diagram showing one embodiment of the invention described herein.

Each of the references cited herein are incorporated by reference in their entirety.

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

As used herein, the term "about" means within 10% of a stated amount.

As used herein, the term "contaminant" or "impurity" is a material that is different from the desired polypeptide product. The contaminant may be a variant or portion of the desired product or another polypeptide or some other fragment or residual from the production process.

As used herein, the term "purification" means removal of contaminant or impurities.

As used herein, the term "rHuEPO" means recombinant human erythropoietin alpha.

As used herein, the term "shelf life" means the amount of time that a product remains viable for use as a human medication under normal storage conditions.

As used herein, the term "isoform" means a glycoprotein preparation that contains glycoproteins which have identical amino acid sequences, but contain distinct isoelectric points. Individual rHuEPO molecules may differ in respect to the complexity, nature and the order of attached glycosyl-, sialyl-, and acetyl groups.

The manufacture of rHuEPO utilizes suitable host cells containing a gene expressing the rHuEPO product. These cells are then cultured in a media and the rHuEPO product is collected for downstream processing. The manufacture of the rHuEPO contains not only the rHuEPO of interest, but significant amounts of impurities, including aggregates, dimers, monomers, and other impurities, from the manufacture of the product. The incorporation of these impurities into a product suitable for subcutaneous injection in to a human patient would prevent the use of this drug, and thus the impurities must be substantially removed. Current products of rHuEPO have a shelf life of approximately 2 years. For the current commercial products, it is not known definitively what causes the short shelf life, and it is likely multi-factorial. As indicated above, the stability of potency of the product needs to be maintained, but the safety of the product needs also to be maintained. There is a well-described phenomena where glass delamination occurs in Type 1 glass vials that is formed in a tubing formation process. Glass delamination is undesirable from a safety perspective and would also be a consideration from a stability perspective—delamination gets worse with time. In our example, Type 1 glass vials that are formed in a moulding formation process are used. This, in addition to the process related impurities, in aggregate, create a scenario for enhanced stability at 2 to 8° C. in a liquid formulation.

Type 1 glass is borosilicate glass known for its stability. It is the least reactive glass, leaches the least amount, and has the lowest pH shift of glass containers. All of these factors are important with regard to the introduction of any contaminants for a product that may be stored for a duration of years. Furthermore, by reducing introduction of contaminants, the safety profile can be improved, regardless of the storage time.

The elimination of these impurities, specifically, those impurities that are able to function and act as a catalyst is critical to ensuring an increased shelf life. Furthermore, the removal of certain isoforms is also important from a potency perspective. It is known that certain isoforms are more potent than others. Potency needs to be maintained from a clinical perspective. A summary of the average isoforms of six simples are included in Table 3b in the Example, and representative sample of all isoforms of one sample is included in Table 3a. rHuEPO has several glycosylation sites, including O-glycosylation at S126 and three N-glycosylation sites at N24, N38, N83. The various isoforms include differing number of sialic acid residues in connection with these glycosylation sites. Each of the different isoforms have different biological activity.

The embodiments disclosed herein provide methods for purifying rHuEPO from a composition comprising the rHuEPO polypeptide and one or more contaminants and for selection of isoforms. The contaminants and the polypeptides of interest are created through the manufacturing process, generally described above. There are numerous variations in the manufacturing process that result in the production of rHuEPO and various contaminants. For improved stability, there is a need to remove impurities (or not add them) to prevent these impurities from serving to catalyze the protein to degrade and lose potency.

The removal of these contaminants is typically performed through one or more purification steps. Prior purification steps have proven to be insufficient at removal of a sufficient amount of impurities, leading to the shelf-life of about 2 years. The methods, as disclosed herein, are improved purification methods that result in an rHuEPO that is bio-similar to approved therapeutic agents while having a superior shelf life as compared to currently available products.

Examples of purification procedures that may be performed on rHuEPO include ultradiafiltration, anion exchange chromatography, cation exchange chromatography, liquid chromatography, ammonium sulfate precipitation, hydrophobic interaction chromatography, reversed phase chromatography, gelfiltration, and nano filtration. Each of these processes function to eliminate certain impurities and together the processes provide for an improved process for purification of rHuEPO.

In view of the Figures, FIG. 1 depicts an embodiment having and eight step process comprising the steps in the following order: anion exchange, ammonium sulfate precipitation, hydrophobic interaction chromatography, reversed phase chromatography, reversed phase chromatography pooling, anion exchange chromatography, gelfiltration for buffer exchange, and nanofiltration for virus removal.

Figure 2:
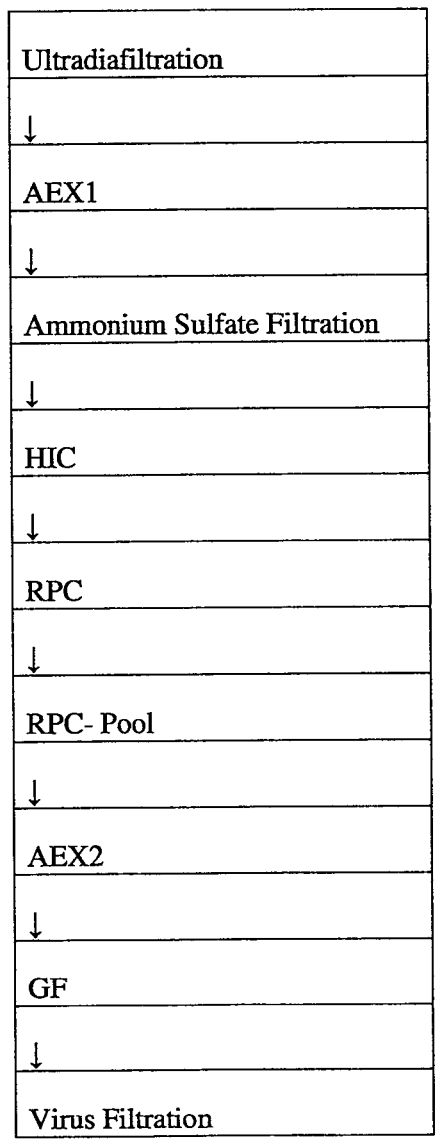
FIG. 2 is a flow diagram showing an alternative embodiment of the invention described herein.

In view of FIG. 2, a further embodiment comprises the following steps in the following order: ultradiafiltration, anion exchange, ammonium sulfate precipitation, hydrophobic interaction chromatography, reversed phase chromatography, anion exchange chromatography, gelfiltration for buffer exchange, and nanofiltration for virus removal.

Figure 3:
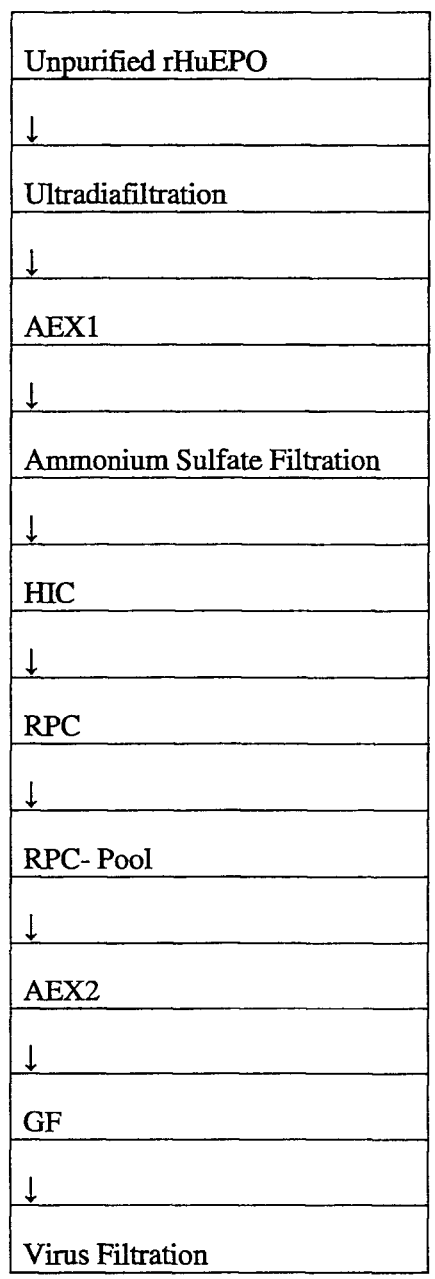
FIG. 3 is a flow diagram showing another alternative embodiment of the invention described herein.

In view of FIG. 3, a further embodiment begins with the manufacture of unpurified rHuEPO and consists of the following steps performed in order: ultradiafiltration, anion exchange, ammonium sulfate precipitation, hydrophobic interaction chromatography, reversed phase chromatography, reversed phase chromatography pooling, anion exchange chromatography, gelfiltration for buffer exchange, and nanofiltration for virus removal.

According to one embodiment of the invention, a method for purification of rHuEPO comprises a purification process comprising the following purification steps in order: ultradiafiltration, anion exchange, ammonium sulfate precipitation, hydrophobic interaction chromatography, reversed phase chromatography, reversed phase chromatography pooling, anion exchange chromatography, gelfiltration for buffer exchange, and nanofiltration for virus removal.

According to another embodiment, the processes follow in order and intend to provide for the purification of rHuEPO in a pure and clean form suitable as a drug substance. The process comprises:
Anion exchange chromatography—separation based on charge, followed by
Ammonium sulfate precipitation—separation based on solubility, followed by
Hydrophobic interaction chromatography—separation based on hydrophobicity, followed by
Reversed phase chromatography—separation based on separation of hydrophobicity and pooling of fractions, followed by
A second anion exchange chromatography—separation based on charge, followed by
Gelfiltration—separation by size, and followed by
Nanofiltration—filtration by size for instance for virus removal.
A further step may be included before the first anion exchange chromatography step:
Ultradiafiltration—separating based on molecular size.

One step in the filtration processes is ultradiafiltration. Ultradiafiltration is a form of tangential flow membrane filtration that utilizes hydrostatic pressure and a semipermeable membrane to separate suspended materials of high molecular weight. Typically, separation of molecules from $10^3$ to $10^6$ Da is achieved. The large molecules that accumulate at the membrane surfaces may then be flushed from the membrane in the diafiltration process, that effectively washes off the collected molecules with additional buffer, while replacing fresh solvent to the feed to replace the permeate volume that is removed. Ultradiafiltration or, also known as, ultra/diafiltration, can be performed using methods and techniques generally known and available to those skilled in the art.

A second step in the filtration process is anion exchange chromatography wherein proteins are separated based on their charges. Anion exchange chromatography, and its counterpart, cation exchange chromatography, includes a stationary phase, a bead or resin, typically, that has a fixed charge. Anion exchange means that the fixed charge is positive. The fixed charge will interact with molecules of opposite charge in the mobile phase. In other words, an anion exchange chromatography will attract negatively charged species from the mobile phase. Thus, if a protein has a negative charge, and is passed through an anion exchange column, it may bind to the matrix. To subsequently elute the bound protein, one may change the ion concentration of the buffer solution, so that the buffer will take the site on the resin and the protein will be eluted from the column.

Processes often utilize buffers comprising guanidine. Urea and guanidine are similar molecules with some similar properties with regard to disrupting or unfolding proteins. Urea is utilized at about 6M, and is further diluted through the processes. Guanidine, like urea, is a denaturant at higher concentrations. At 6M, guanidine HCl is known to disrupt secondary structures of proteins. Use of guanidine HCl or other salt at 3M, 1M, 0.5M, and 0.1M provides for less interaction with the proteins. At certain low concentrations of guanidine, there is a hypothesis that misfolded proteins, impurities, etc. are slightly denatured to enable washing steps to be more effective. Essentially, the guanidine preferentially attacks unglycosylated proteins, small proteins, and/or hydrophobic proteins, all of which tend to be impurities. Guanidine may denature small proteins effectively that could act as catalysts. Accordingly, by utilizing such a buffer, there is a preferential attack on these impurities, which are then removed through the anion exchange process. However, urea, as utilized herein advantageously attacks certain proteins for improving removal.

In particular, anion exchange chromatography is used as a step in a process for purifying rHuEPO in a downfield purification sequence. Proteins are charged molecules and thus anion exchange chromatography can effectively be utilized to separate certain proteins based on their molecular charge. Anion exchange further relies upon the pH of a buffer to be between the isoelectric point or pKa (acid dissociation constant) of the charged molecule and the pKa of the charged group on the solid support. For example, a molecule with a pH of 6.8 and where the pKa of the solid support is 10, would utilize a buffer that is between 6.8 and 10. Furthermore, the use of salt gradient, that is, a linearly increasing salt concentration is utilized to elute the sample components from the column. Alternatively, a step gradient can be utilized, as is known in the art. Many chromatography processes also vary the pH to affect separation, for example, lowering the pH of the mobile phase will cause the molecule to become more protonated and hence more positively charged. As the positive charge of the molecules increase, the protein can no longer form an ionic interaction with the positively charged support allowing the molecules to elute from the column.

A further step in the purification process is ammonium sulfate precipitation. Ammonium sulfate precipitation, is a method of protein purification that utilizes alterations in solubility to precipitate out proteins from a solution. The basic idea is to allow for the protein of interest to be precipitated out of solution while leaving the majority of contaminants still in the solution. Furthermore, this technique is utilized to concentrate protein from a dilute solution, where the precipitate is collected and recovered by centrifugation, before dissolving in fresh buffer or other solution. This allows for not only a mechanism for purification, but for manipulation of concentration and buffer supporting the protein.

A further step in the purification process is hydrophobic interaction chromatography. Hydrophobic interaction chromatography (HIC) is a separation technique based on the reversible interaction between a protein and the hydrophobic ligand bound to a chromatography matrix. Proteins have hydrophobic areas on their surface and the promotion of the hydrophobic effect (through the addition of salts) drives the adsorption of the hydrophobic areas on a protein to the hydrophobic areas on the solid support. HIC is well suited for use with buffers with high ion strength, therefore, its use as a secondary purification step after either ammonium sulfate precipitation or after elution in high salt ion exchange chromatography is particularly suited. Accordingly, HIC binds proteins at high salt concentrations and elutes them through buffers having lower salt concentrations and using a decreasing salt gradient allowing for separation of different proteins.

A further purification step is reverse phase chromatography. Reverse phase chromatography is a form of hydrophobic interaction chromatography in which hydrophobic molecules interact with each other rather than interact with water molecules. The "reverse phase" means that the molecules are bound to a hydrophobic matrix in a buffer of hydrophilic buffer and eluted from the column by reducing the polarity of the buffer (typically though the addition of alcohol to the water). This process is typically used to separate small molecules. The beads, or the stationary phase in the column, consist of hydrophobic molecules, such as long chain hydrocarbons that are bound to a silica matrix. Non-polar or hydrophobic molecules in the mobile phase will bind to the matrix. These bound molecules can then be eluted by decreasing the polarity of the buffer, through the addition of an alcohol or another non-polar solvent into the buffer.

The separation of isoforms occurs in the reverse phase step, as depicted in the Figures as RPC-Pool. During the elution of the product, various fractions are taken and assessed for isoform distribution. A mathematical formula is used to weight/calculate the additions in order to hit the target profile. The appropriate volume fractions are pooled and taken through the remainder of the process.

A further purification process is gel filtration. Gel filtration for buffer exchange, also referred to as molecular exclusion chromatography, takes molecules in solution and separates them by size as they pass through a column of cross-linked beads which are organized in a three-dimensional network. The beads have pores of a specific size in them, allowing for certain sized molecules to enter the pores. As a sample passes through the column, the molecules can take one of two routes, depending on their size. The molecules smaller than the bead pores will enter the pores and thus move slowly through the column, while larger molecules will not enter the pores and so will elute from the column first where after samples are then typically collected in fractions. Gel filtration not only provides a purification and filtration step, but also allows for the exchange of buffer solutions.

A further purification step is nanofiltration. Nanofiltration utilizes a 0.1 μm filter for removal of viruses from the remaining solution. Essentially, the filtration process allows for separation of small and larger molecules by diffusion through the small membrane. In this manner, viruses that may be present due to the upstream manufacture of the rHuEPO glycoprotein can be substantially removed from the product.

According to other embodiments of the invention, a method for filtration may comprise anion exchange, ammonium sulfate precipitation, hydrophobic interaction chromatography, reversed phase chromatography, anion exchange chromatography, gelfiltration for buffer exchange, nanofiltration for virus removal.

Each of the various chromatography and purification steps can be performed by processes generally known by persons of ordinary skill in the art.

Further embodiments of the invention comprise a method for filtration comprising the followings steps in sequential order: anion exchange chromatography, ammonium sulfate precipitation, hydrophobic interaction chromatography, reversed phase chromatography, anion exchange chromatography, and gelfiltration for buffer exchange.

Further embodiments of the invention comprise a method for filtration comprising the followings steps: anion exchange, ammonium sulfate precipitation, hydrophobic interaction chromatography, reversed phase chromatography, and anion exchange chromatography. The resulting product may then be further processed by various means for viral removal or inactivation and loaded into Type 1 glass vials under conditions suitable to maintain the cleanliness of the product to provide a rHuEPO product having an enhanced stability profile.

Example 1: Process for Purifying rHuEPO

Anion Exchange
Materials:
UDF1 UDR 0.2 μm
HQ-water
EQ-buffer—20 mM TRIS/20 μM $CuSO_4$ pH 7.5
NW1-buffer—6 M Urea/1 mM Glycine/6 mM acetic acid/20 μM $CuSO_4$p16 mM NaCl
Elution buffer—20 mM TRIS/180 mM NaCl/20 μM $CuSO_4$ pH 8.5
1 M NaCl
20% EtOH
0.01 M NaOH
1 M NaOH
Materials and Equipment
　Chromatography Medium—DEAE-Sepharose FF—GE Healthcare
　Chromatography Column: inner diameter 350 mm—Millipore
　Chromatography system: K-Prime—Millipore
　pH-meter and electrode
　Misc. parts: tube connectors and parts made of polypropylene, silicon tubing, glass bottle, stainless steel tank, pH paper, conductivity meter and sensor, balance, and magnetic stirrer Calculation:
The density of all solution is considered to be 1 g/cm$^3$. Thus, determination of volumes can be performed by weight. The area of the chromatography column results from internal diameter (d—35 cm) A [cm$^2$]=r$^2$ [cm$^2$]×π=(35/2)$^2$×π=962.1 [cm$^{2\pi}$]
Flow rate=3528 ml/min
Procedure:
　Column dimension: max 25 mg rHuEPO/ml DEAE-Sepharose Fast Flow
　Gel Volume: 21.5 L±20% (corresponds to 17.9-26.8 cm bed height)
　Column inner diameter: 350 mm
　Packing quality is tested by HETP and asymmetry
　Chromatographic gel is not used for more than 9 cycles

| Step | min. flow rate [cm/h] | min flow rate [l/min] | max flow rate [cm/h] | max flow rate [l/min] |
|---|---|---|---|---|
| Depyrogenation, equilibration, loading, washing, regeneration, storage | 50 | 0.80 | 220 | 3.53 |
| Washing 1, washing 2 | 50 | 0.80 | 220 | 3.21 |
| Elution | 31 | 0.50 | 100 | 1.60 |

Conditioning, regeneration, and equilibration
1. Flush the column with at least 0.5 GV (Gel volumes) of EQ-Buffer at a target flow rate of min. 0.80 l/min and max 3.53 l/min.
2. Regenerate the column with at least 1.5 GV of 1 M NaCl at a target flow rate of min. 0.80 l/min and max 3.53 l/min
3. Equilibrate the column with at least 1.5 GV of EQ-buffer at a target flow rate of min 0.80 l/min and max 3.53 l/min
4. Determine conductivity and pH at the column outlet (external measurement), limits are 7.3-7.7 for pH and 1.3-1.7 mS/cm for conductivity.
5. Adjust base line on the k-Prime chromatography system when measure values are within these set limits.
6. Load rHuEPO to be filtered.
Loading, washing, washing 1, and washing 2
1. Starting with a sample medium containing rHuEPO, Load the rHuEPO to be filtered with a target flow rate of min 0.80 l/min and max 3.53 l/min. A significant increase of the process pressure may occur which has to be eliminated by a decrease of the flow rate.
2. Collect fraction AEX DL+NW when $OD_{280nm}$ increases to approx. 0.25. End fraction collection when column was washed with 1 GV of EQ-buffer.
3. Wash column with at least 4 GV of EQ-buffer with a target flow rate of min 0.80 l/min and max 3.53 l/min. If process pressure has increased during loading it should clearly decrease after approximately 1 GV. Thus, flow rate can be increased again.
4. Wash the column with 2 GV of W1-buffer, with a target flow rate of min 0.80 l/min and max 3.53 l/min. A clear increase of the process pressure may occur which has to be eliminated by a decrease of the flow rate.
5. Collect fraction AEX1 NW1 when 0.75 CV W1-buffer were washed or $OD_{280nm}$ increases to approximately 0.25. Fraction collection can be ended when signal drops back to approximately 0.25.
6. Remove W1-buffer from column by applying at least 4 GV of EQ-buffer with a target flow rate of min 0.80 l/min and max 3.53 l/min.

Elution:
1. Elution is performed with elution buffer with a target flow rate of min 0.50 L/min and max 1.60 l/min.
2. Collect eluate when OD280 nm increases to approximately 7.0 or after achieving the peak maximum and the latest.
3. End elution manually when at least 2.5 GV of eluate have been collected and the OD280 nm has dropped back to approximately 0.4.

Ammonium Sulfate Precipitation
1. AEX1 eluate and AS-buffer—20 mM TRIS/3.6 M $(NH_4)_2SO_4$ pH 7.5.
2. Density of AEX1 eluate is considered to be 1 g/cm3—Density of the AS-buffer is 1.215 g/cm3 and the ammonium sulfate concentration is 3.6 M. The final concentration of ammonium sulfate in the precipitation is 2.0 M—Calculation of the required amount of AS-buffer for 1 ml AEX1 eluate is 1.520 g.

Procedure:
1. Add the required amount of AS-buffer to the AEX1 eluate. Addition is performed while stirring over a period of 30 minutes to prevent localized high concentrations. —continue stirring for 30-60 additional minutes.
2. Determine pH and conductivity of the sample. Limits pH 7.3-7.7, conductivity 215-250 mS/cm.
3. Let the sample settle for 2-24 hours at room temperature. After settlement of the precipitate, manipulations of the tank should be avoided to prevent dispersion of the precipitation.
4. Filter the ammonium sulfate precipitation across a 0.2 μm filter. The main focus is on the separation of the precipitate not on the 0.2 μm filtration of the product.
5. Collect the ammonium sulfate filtrate.

Hydrophobic Interaction Chromatography
Materials:
Chromatography medium—Phenyl-Sepharose 6FF (low sub)—GE Healthcare
Chromatography System—K-Prime—Millipore
Flow rate of 1767 ml/min
Procedure:
Column dimension: max. 35 mg rHuEPO/ml Phenyl-Sepharose 6FF
Gel volume 12.5 l±20% (corresponds to 14.1 to 21.2 cm bed height)
Column internal diameter: 300 mm

| Step | min. flow rate [cm/h] | max flow rate [l/min] | max. flow rate [cm/h] | max. flow rate [l/min] |
|---|---|---|---|---|
| Depyrogenation, equilibration, loading, washing, regeneration, storage | 17 | 0.20 | 150 | 1.77 |
| Elution | 17 | 0.20 | 100 | 1.18 |

Regeneration and equilibration—Regenerate the column if it was previously stored. Equilibrate the column with at least 1.5 GV of EQ-buffer at a target flow rate of 0.20-1.77 l/min. Determine pH and conductivity at column outlet. Limits are 7.3-7.7 pH and 215-240 mS/cm for conductivity. Adjust the base line on K-Prime chromatography system and turn on external writer and adjust baseline on the UV-cell. Set sensitivity of the cell to 0.2 AU. Begin loading of filtrate from ammonium sulfate precipitation after writer achieves stable baseline.

1. Load ammonium sulfate filtrate with a target flow rate of 0.20-1.77 l/min.
2. Collect fraction ICH DL+NW when OD280 nm increases to approximately 0.25. End fraction collection when column has been washed with 2 GV of EQ-buffer.
3. Wash column
4. Elute column with elution buffer at a target flow rate of 0.20 to 1.18 l/min. Collect eluate when a significant increase of OD280 nm can be observed (at approximately 0.5 OD on K-Prime or 15-30% of maximum amplitude at a sensitivity of 0.2 AU).
5. End Eluate collection at 0.25 OD or after approximately 2.9 GV
6. Regenerate the column with at last 1.5 GV of REG-buffer at a target flow rate of 0.20-1.77 l/min and immediately collect fraction REG.
7. REG collection can be ended when baseline drops back to approximate baseline (0.25 OD according to K-Prime).

Reverse Phase Chromatography
Materials:
HIC eluate, HQ-water
Dilution buffer—20 nM TRIS pH 7.5
Buffer A—20 nM Tris/25% acetonitrile pH 7.0
Buffer B—Tris/50% acetonitrile pH 7.0
Mixing buffer 50 mM Tris pH 7.0
20% EtOH
1 M NaOH
Chromatography medium: SOURCE 30 RPC—GE Healthcare
Chromatography column: inner diameter 300 mm—Millipore
Chromatography system: K-Prime—Millipore
Flow rate 3535 ml/min
Procedure:
The HIC eluate is diluted 1+5 in two steps. First step is to dilute the HIC eluate with dilution buffer in a weight ration of 1+2 to reduce the conductivity. The diluted HIC eluate is further diluted in a volume ration of 1+1 with buffer B to increase the acetonitrile concentration to 25%. The conductivity of this RPC load must not exceed 35 mS/cm prior to loading onto column. Conductivity higher than 35 mS/cm the product may not bind on to column.
Viral inactivation—incubate the solution for 5-10 minutes in an acetonitrile concentration of 25%. pH and conductivity must be confirmed at start and end of incubation with limits of 6.8-7.7 pH and <35 mS/cm for conductivity.
The column is equilibrated and the RPC load is loaded with a target flow rate of 0.80 3.53 l/min. Flow through as to be collected in a waste vessel as solutions containing acetonitrile have to be disposed of separately. After loading is completed, purge with at least 3 GV of buffer A at a flow rate of 0.8-3.53 l/min. Signal must drop back to approximate baseline.
Elution:
The elution is performed by applying an acetonitrile gradient that is increased from 25% to 50% during application of 15 GV. This corresponds to a process gradient of 0-100% buffer B which is mixed online with buffer A. The eluate fractions are collected in vessels containing the 3-folds amount of mixing buffer thus immediately decreasing the acetonitrile concentration by a factor of 4. Start the elution gradient as described above at a target flow rate of 0.80-2.59 l/min. Collect eluate in fractions of approximately 0.25 GV (0.125 GV in case only one product harvest is processed) when a significant increase of OD280 nm is observable (approximately 0.5 OD according to K-Prime).

Second Anion Exchange Chromatography
Materials:
RPC Pool
Dilute RPC Pool with HQ-Water in a 1+1 ratio—determine conductivity and pH of the diluted RPC Pool, limits are 6.8-7.7 pH and ≤2.0 mS/cm for conductivity. If conductivity is too high, HQ water has to be added until the limit is met.
Procedure:
Equilibrate the column with at least 1.5 GV EQ—buffer at a target flow rate of 111-664 ml/min. Adjust baseline on the chromatogram if an external writer of UV-monitor is used. Determine pH and conductivity at column outlet. Limits are 7.3-7.7 pH and 1.3-1.7 mS/cm for conductivity. Adjust base line on the K-Prime chromatography system when measured values are within these limits. Load diluted RPC Pool at a target flow rate of 111-664 ml/min. Flow through (contains acetonitrile) is collected and discarded. After completion of loading flush with at least 4 GV of EQ-buffer-SFI at a target rate of 111-664 ml/min. After 2 GV have been flushed waste collection is no longer necessary. Elution is performed with elution buffer at a target flow rate of 111-664 ml/min. Collect elute when a significant increase of OD280 nm (10-20% of writer's maximum amplitude at a sensitivity of 0.2 AU or 0.2 OD according to K-Prime) is observable. The eluate collection has to be ended at the latest at 20% of writer's maximum amplitude when sensitivity is set to 0.2 AU (10% above baseline—end of elution or 0.1 OD according to K-Prime).

Gelfiltration:
Materials:
AEX2 Elute
Chromatography medium: Sephadex %25 coarse—GE Healthcare
Chromatography column: inner diameter 250 mm—Millipore
Chromatography system K-Prime
Column dimension: max 0.25 ml loading volume/mi Sephadex G25 coarse—gel volume 15 l±25% (corresponding to 22.9 to 38.2 cm bed height).

Flow Rate:

| Step | min. flow rate [cm/h] | max flow rate [l/min] | max. flow rate [cm/h] | max. flow rate [l/min] |
|---|---|---|---|---|
| All steps | 100 | 0.82 | 300 | 2.45 |

Procedure:
Equilibrate the column with at least 4 GV of EQ-buffer at a target flow rate of 0.82-2.45 l/min. Determine conductivity and pH at column outlet (external measurement). Limits are 6.8-7.2 for pH and 12.5-15.5 mS/cm for conductivity. Adjust baseline on the K-Prime chromatography system when measured values are within these limits. Begin loading ZEX2 eluate.
Load the AEX2 eluate with a target flow rate of 0.82-2.45 l/min. Load not more than 0.25 mil eluate per ml of Sephadex ˆ25 coarse. After loading, wash the column with EQ buffer—WFI at a target flow rate of 0.82-2.45 l/min. Collect eluate when OD280 nm increases to approximately 0.1. Elution is complete when OD280 nm drops back to Approximately 0.05.

Virus Filtration:
Materials:
Begin with the Gel Filtration Eluate.
Buffer 20 mM citric acid/100 mM NaCl pH 7.0 (WFI)
0.1 μm membrane filter—e.g. Sartopore 2 cat. no 5445358K7SS
Virus Filter—E.g. Sartorius 20 nM Virosart CPV, 0.2 m² cat. no 5455328V9
Procedure:
The product concentration during virus filtration should be approximately 3.5 mg/ml. Therefore the GF eluate is diluted with buffer. The diluted gel filtrate is filtered across a 0.1 μm filter. Virus filtration requires that the 0.1 μm filter is coupled to the pressure tank and coupled to the virus filter. The pressure tank is filled with buffer and then used to flush the filters at a pressure of 2.0 bar. The filters are purged empty and pressure is released using the vent screw on the air filter. Only the 0.1 μm filter can be completely emptied.
Not more than 22 l can be filtered per capsule. The filtrate is added to the pressure tank, the vent screws on the 0.1 μm filter and the virus filter are opened to allow venting. The vent screws are closed when air has been completely removed. The pressure is adjusted to 2.0 bar and the filtrate is filtered across the two filters. The filer can then be purged and flushed. The product concentration in the virus filtrate is determine ($OD_{280}$) and the concentration is adjusted to 2.5±1 mg/ml with the addition of buffer.
After collection and adjustment of the concentration of the filtrate, the rHuEPO product is ready for storage or use.
The procedure outlined in Example 1 was utilized to create a number of batches. These batches create a rHuEPO product having a concentration of 2.5±1.0 mg/ml stored at 2-8° C. Stability testing was then performed on at least six batches, wherein each individual batch was analyzed at time points 0, 3, 6, 9, 12, 18, 24, 36, 48, 60, and 72 months for the following parameters (unless noted):
Content (OD280 nm)
CZE (Capillary Zone Electrophoresis)—For determination of isoforms
SEC (Size Exclusion Chromatography)
SDS-PAGE (Sodium dodecyl sulfate polyacrylamide gel electrophoresis)
Western Blot
SIA (Sialic Acids)
Biological Activity (in-vivo bioassay)
Visual Appearance
pH and osmolality
Sterility (Excluding time points 3 m, 6 m, 9, and 18 m)
Endotoxin (Excluding time points 3 m, 6 m, 9, and 18 m)

TABLE 1

| Summary of batch analysis | | | | | | | | | | | |
|---|---|---|---|---|---|---|---|---|---|---|---|
| Method | 0 M | 3 M | 6 M | 9 M | 12 M | 18 M | 24 M | 36 M | 48 M | 60 M | 72 M |
| Content | x | x | x | x | x | x | x | x | x | x | x |
| CZE | x | x | x | x | x | x | x | x | x | x | x |
| SEC | x | x | x | x | x | x | x | x | x | x | x |

TABLE 1-continued

Summary of batch analysis

| Method | 0 M | 3 M | 6 M | 9 M | 12 M | 18 M | 24 M | 36 M | 48 M | 60 M | 72 M |
|---|---|---|---|---|---|---|---|---|---|---|---|
| SDS-PAGE | x | x | x | x | x | x | x | x | x | x | x |
| Western Blot | x | x | x | x | x | x | x | x | x | x | x |
| SIA | x | x | x | x | x | x | x | x | x | x | x |
| Biological Activity | x | x | x | x | x | x | x | x | x | x | x |
| Visual Appearance | x | x | x | x | x | x | x | x | x | x | x |
| pH and Osmolality | x | x | x | x | x | x | x | x | x | x | x |
| Sterility | x | | | x | | x | x | x | x | x | x |
| Endotoxin | x | | | x | | x | x | x | x | x | x |

Data was then collected with regard to each of the six batches that were tested. The following batch numbers were tested: T69, T70, T72, T76, T77, and T78. These batch numbers are utilized in the following Tables.

TABLE 2

Content (OD280 nm)

| Time-point | T69 | T70 | T72 | T76 | T77 | T78 | Lower limit | upper limit | Unit |
|---|---|---|---|---|---|---|---|---|---|
| 0 M | 2.38 | 2.50 | 2.47 | 2.62 | 2.51 | 2.47 | 1.5 | 3.5 | mg/ml |
| 3 M | 2.37 | 2.41 | 2.48 | 2.45 | 2.41 | 2.35 | 1.5 | 3.5 | mg/ml |
| 6 M | 2.44 | 2.49 | 2.53 | 2.49 | 2.42 | 2.41 | 1.5 | 3.5 | mg/ml |
| 9 M | 2.37 | 2.39 | 2.37 | 2.44 | 2.11 | 2.33 | 1.5 | 3.5 | mg/ml |
| 12 M | 2.31 | 2.37 | 2.44 | 2.42 | 2.37 | 2.36 | 1.5 | 3.5 | mg/ml |
| 18 M | 2.34 | 2.37 | 2.45 | 2.50 | 2.38 | 2.38 | 1.5 | 3.5 | mg/ml |
| 24 M | 2.27 | 2.30 | 2.39 | 2.58 | 2.44 | 2.45 | 1.5 | 3.5 | mg/ml |
| 36 M | 2.30 | 2.32 | 2.39 | 2.42 | 2.31 | 2.34 | 1.5 | 3.5 | mg/ml |
| 48 M | 2.26 | 2.28 | 2.37 | 2.51 | 2.37 | 2.41 | 1.5 | 3.5 | mg/ml |
| 60 M | 2.31 | 2.37 | 2.38 | | | | 1.5 | 3.5 | mg/ml |

TABLE 3a

CZE individual isoform percentage for T72

| Timepoint Unit | IF1 % | EF2 % | IF2 % | IF4 % | IF5 % | IF6 % | IF7 % | IF8 % | IF9 % |
|---|---|---|---|---|---|---|---|---|---|
| Lower limit | 0 | 0 | 0 | 1 | 15 | 25 | 15 | 1 | — |
| Upper limit | 20 | 20 | 20 | 20 | 35 | 45 | 35 | 20 | — |
| 0 M | 0 | 0 | 0 | 2 | 25 | 43 | 26 | 4 | 0 |
| 3 M | 0 | 0 | 0 | 3 | 24 | 42 | 26 | 4 | 0 |
| 6 M | 0 | 0 | 0 | 4 | 25 | 41 | 26 | 5 | 0 |
| 9 M | 0 | 0 | 1 | 3 | 25 | 42 | 26 | 4 | 1 |
| 12 M | 0 | 0 | 0 | 1 | 25 | 44 | 29 | 2 | 0 |
| 18 M | 0 | 0 | 0 | 3 | 26 | 42 | 26 | 4 | 0 |
| 24 M | 0 | 0 | 0 | 2 | 26 | 44 | 27 | 3 | 0 |
| 36 M | 0 | 0 | 0 | 3 | 26 | 42 | 26 | 3 | 0 |
| 48 M | 0 | 0 | 0 | 2 | 26 | 45 | 25 | 3 | 0 |
| 60 M | 0 | 0 | 0 | 2 | 24 | 42 | 27 | 5 | 0 |

TABLE 3b

CZE weighted average for six samples
This represents the average of Isoforms 1-9 in each sample.

| Timepoint | T69 | T70 | T72 | T76 | T77 | T78 | Unit |
|---|---|---|---|---|---|---|---|
| 0 M | 6.02 | 6.04 | 6.02 | 5.94 | 5.85 | 6.02 | — |
| 3 M | 6.00 | 6.05 | 6.01 | 5.95 | 5.88 | 6.04 | — |
| 6 M | 6.09 | 6.03 | 6.01 | 5.98 | 5.89 | 6.03 | — |
| 9 M | 6.04 | 6.04 | 6.01 | 5.98 | 5.93 | 5.97 | — |
| 12 M | 6.10 | 6.06 | 6.02 | 5.99 | 5.97 | 6.07 | — |
| 18 M | 6.07 | 6.04 | 6.04 | 5.98 | 5.99 | 5.96 | — |
| 24 M | 6.04 | 6.03 | 5.99 | 5.92 | 5.87 | 5.95 | — |
| 36 M | 6.02 | 6.01 | 5.99 | 5.95 | 5.95 | 5.91 | — |
| 48 M | 6.05 | 6.01 | 5.98 | 5.98 | 5.88 | 6.02 | — |
| 60 M | 6.03 | 6.07 | 6.00 | | | | — |

TABLE 4

Purity/Dimers and multimers (SEC-HPLC)

| Time-point | T69 | T70 | T72 | T76 | T77 | T78 | Lower limit | upper limit | Unit |
|---|---|---|---|---|---|---|---|---|---|
| 0 M | 0.95 | 0.61 | 0.35 | 0.97 | 1.23 | 0.64 | 0 | 2 | % |
| 3 M | 1.05 | 0.81 | 0.91 | 0.59 | 1.41 | 1.03 | 0 | 2 | % |
| 6 M | 0.73 | 0.62 | 0.60 | 0.49 | 1.14 | 0.73 | 0 | 2 | % |
| 9 M | 0.96 | 0.62 | 0.52 | 0.42 | 0.81 | 0.50 | 0 | 2 | % |
| 12 M | 1.10 | 0.63 | 0.63 | 0.24 | 0.91 | 0.60 | 0 | 2 | % |
| 18 M | 0.87 | 0.56 | 0.61 | 0.53 | 1.15 | 1.02 | 0 | 2 | % |
| 24 M | 0.73 | 0.45 | 0.34 | 0.61 | 1.07 | 0.76 | 0 | 2 | % |

TABLE 4-continued

Purity/Dimers and multimers (SEC-HPLC)

| Time-point | T69 | T70 | T72 | T76 | T77 | T78 | Lower limit | upper limit | Unit |
|---|---|---|---|---|---|---|---|---|---|
| 36 M | 1.17 | 0.61 | 0.38 | 0.76 | 1.18 | 0.81 | 0 | 2 | % |
| 48 M | 1.08 | 0.72 | 0.79 | 1.24 | 1.62 | 1.35 | 0 | 2 | % |
| 60 M | 0.90 | 0.69 | 0.83 | | | | 0 | 2 | % |

TABLE 5

SDS-PAGE

| Timepoint | T69 | T70 | T72 | T76 | T77 | T78 | Unit |
|---|---|---|---|---|---|---|---|
| 0 M | pass | pass | Pass | pass | pass | pass | — |
| 3 M | pass | pass | Pass | pass | pass | pass | — |
| 6 M | pass | pass | Pass | pass | pass | pass | — |
| 9 M | pass | pass | Pass | pass | pass | pass | — |
| 12 M | pass | pass | Pass | pass | pass | pass | — |
| 18 M | pass | pass | Pass | pass | pass | pass | — |
| 24 M | pass | pass | Pass | pass | pass | pass | — |
| 36 M | pass | pass | Pass | pass | pass | pass | — |
| 48 M | pass | pass | Pass | pass | pass | pass | — |
| 60 M | pass | pass | Pass | | | | — |

TABLE 6

Western Blot

| Timepoint | T69 | T70 | T72 | T76 | T77 | T78 | Unit |
|---|---|---|---|---|---|---|---|
| 0 M | pass | pass | Pass | pass | pass | pass | — |
| 3 M | pass | pass | Pass | pass | pass | pass | — |
| 6 M | pass | pass | Pass | pass | pass | pass | — |
| 9 M | pass | pass | Pass | pass | pass | pass | — |
| 12 M | pass | pass | Pass | pass | pass | pass | — |
| 18 M | pass | pass | Pass | pass | pass | pass | — |
| 24 M | pass | pass | Pass | pass | pass | pass | — |
| 36 M | pass | pass | Pass | pass | pass | pass | — |
| 48 M | pass | pass | Pass | pass | pass | pass | — |
| 60 M | pass | pass | Pass | | | | — |

TABLE 7

Sialic Acids (SIA)

| Time-point | T69 | T70 | T72 | T76 | T77 | T78 | Lower Limit | Upper Limit | Unit |
|---|---|---|---|---|---|---|---|---|---|
| 0 M | 13.9 | 13.1 | 13.5 | 11.7 | 12.3 | 13.0 | 10 | 14 | mole/mole |
| 3 M | 13.5 | 14.1 | 14.0 | 12.2 | 11.8 | 11.8 | 10 | 14 | mole/mole |
| 6 M | 12.4 | 12.4 | 12.4 | 11.5 | 12.0 | 11.5 | 10 | 14 | mole/mole |
| 9 M | 12.3 | 12.2 | 12.6 | 11.8 | 10.7 | 11.7 | 10 | 14 | mole/mole |
| 12 M | 12.2 | 11.6 | 12.8 | 11.8 | 12.7 | 12.5 | 10 | 14 | mole/mole |
| 18 M | 12.8 | 12.9 | 13.1 | 12.4 | 12.7 | 12.9 | 10 | 14 | mole/mole |
| 24 M | 11.4 | 11.2 | 12.3 | 12.0 | 13.0 | 13.8 | 10 | 14 | mole/mole |
| 36 M | 11.9 | 12.2 | 12.1 | 11.7 | 13.7 | 12.8 | 10 | 14 | mole/mole |
| 48 M | 11.6 | 12.2 | 11.8 | 10.2 | 13.6 | 13.5 | 10 | 14 | mole/mole |
| 60 M | 12.3 | 12.4 | 12.3 | | | | 10 | 14 | mole/mole |

Timepoints 0 and 3 months for batches T69, T70 and T72 were the first batches where this method was not fully validated. The values for these two timepoints are probably overestimated.

TABLE 8

Biological Activity (in-vivo Bioassay)

| Time-point | T69 | T70 | T72 | T76 | T77 | T78 | Lower Limit | Upper Limit | Unit |
|---|---|---|---|---|---|---|---|---|---|
| 0 M | 104900 | 104900 | 110900 | 113500 | 105500 | 109200 | 92000 | 143750 | IU/mg |
| 3 M | 129450 | 107800 | 129500 | 111500 | 120900 | 102300 | 92000 | 143750 | IU/mg |
| 6 M | 105400 | 105150 | 115900 | 116900 | 105000 | 114400 | 92000 | 143750 | IU/mg |
| 9 M | 122900 | 106400 | 112200 | 108600 | 94900 | 108500 | 92000 | 143750 | IU/mg |
| 12 M | 135700 | 114200 | 110200 | 113300 | 109900 | 119200 | 92000 | 143750 | IU/mg |
| 18 M | 129100 | 110100 | 113700 | 117200 | 17800 | 119300 | 92000 | 143750 | IU/mg |
| 24 M | 111300 | 105200 | 118800 | 112900 | 105200 | 132700 | 92000 | 143750 | IU/mg |
| 36 M | 121300 | 109500 | 135800 | 98500 | 99400 | 96800 | 92000 | 143750 | IU/mg |
| 48 M | 114100 | 114500 | 115300 | 118600 | 123800 | 119000 | 92000 | 143750 | IU/mg |
| 60 M | 116600 | 118500 | 131800 | | | | 92000 | 143750 | IU/mg |

TABLE 9 pH

| Time-point | T69 | T70 | T72 | T76 | T77 | T78 | Lower Limit | Upper Limit | Unit |
|---|---|---|---|---|---|---|---|---|---|
| 0 M | 7.0 | 7.0 | 7.0 | 7.0 | 7.0 | 6.8 | 6 | 8 | — |
| 3 M | 7.0 | 7.1 | 7.0 | 6.9 | 6.8 | 6.9 | 6 | 8 | — |
| 6 M | 6.8 | 6.8 | 6.8 | 6.9 | 6.9 | 7.0 | 6 | 8 | — |
| 9 M | 6.9 | 6.9 | 6.9 | 6.9 | 7.0 | 7.0 | 6 | 8 | — |
| 12 M | 6.9 | 6.9 | 6.9 | 6.9 | 6.9 | 6.9 | 6 | 8 | — |
| 18 M | 6.8 | 6.8 | 6.8 | 6.9 | 6.9 | 7.0 | 6 | 8 | — |
| 24 M | 6.8 | 6.9 | 6.9 | 7.0 | 7.0 | 7.0 | 6 | 8 | — |
| 36 M | 6.8 | 6.8 | 6.8 | 6.9 | 6.9 | 6.9 | 6 | 8 | — |
| 48 M | 6.8 | 6.8 | 6.8 | 6.9 | 6.9 | 6.9 | 6 | 8 | — |
| 60 M | 6.8 | 6.8 | 6.8 | | | | 6 | 8 | — |

TABLE 10

Osmolality

| Time-point | T69 | T70 | T72 | T76 | T77 | T78 | Lower Limit | Unit |
|---|---|---|---|---|---|---|---|---|
| 0 M | N/A | N/A | N/A | 257 | 252 | 249 | 220 | mOsmol/kg |
| 3 M | 240 | 246 | 246 | 251 | 245 | 247 | 220 | mOsmol/kg |
| 6 M | 240 | 245 | 242 | 251 | 251 | 250 | 220 | mOsmol/kg |
| 9 M | 238 | 238 | 235 | 253 | 227 | 247 | 220 | mOsmol/kg |
| 12 M | 245 | 242 | 24 | 254 | 251 | 251 | 220 | mOsmol/kg |
| 18 M | 245 | 243 | 241 | 256 | 256 | 250 | 220 | mOsmol/kg |
| 24 M | 242 | 240 | 238 | 255 | 253 | 251 | 220 | mOsmol/kg |
| 36 M | 250 | 251 | 251 | 258 | 255 | 253 | 220 | mOsmol/kg |
| 48 M | 242 | 244 | 244 | 252 | 250 | 250 | 220 | mOsmol/kg |
| 60 M | 237 | 241 | 237 | | | | 220 | mOsmol/kg |

TABLE 11

Visual appearance

| Time-point | T69 | T70 | T72 | T76 | T77 | T78 |
|---|---|---|---|---|---|---|
| 0 M | clear, colorless | clear, colorless | clear, colorless | clear, colorless | clear, colorless | clear, colorless |
| 3 M | clear, colorless | clear, colorless | clear, colorless | clear, colorless | clear, colorless | clear, colorless |
| 6 M | clear, colorless | clear, colorless | clear, colorless | clear, colorless | clear, colorless | clear, colorless |
| 9 M | clear, colorless | clear, colorless | clear, colorless | clear, colorless | clear, colorless | clear, colorless |
| 12 M | clear, colorless | clear, colorless | clear, colorless | clear, colorless | clear, colorless | clear, colorless |
| 18 M | clear, colorless | clear, colorless | clear, colorless | clear, colorless | clear, colorless | clear, colorless |
| 24 M | clear, colorless | clear, colorless | clear, colorless | clear, colorless | clear, colorless | clear, colorless |
| 36 M | clear, colorless | clear, colorless | clear, colorless | clear, colorless | clear, colorless | clear, colorless |
| 48 M | clear, colorless | clear, colorless | clear, colorless | clear, colorless | clear, colorless | clear, colorless |
| 60 M | clear, colorless | clear, colorless | clear, colorless | clear, colorless | clear, colorless | clear, colorless |

TABLE 12

Sterility

| Timepoint | T69 | T70 | T72 | T76 | T77 | T78 |
|---|---|---|---|---|---|---|
| 0 M | sterile | sterile | sterile | sterile | sterile | sterile |
| 12 M | sterile | sterile | sterile | sterile | sterile | sterile |
| 24 M | sterile | sterile | sterile | sterile | sterile | sterile |
| 36 M | sterile | sterile | sterile | sterile | sterile | sterile |
| 48 M | sterile | sterile | sterile | sterile | sterile | sterile |
| 60 M | sterile | sterile | sterile | sterile | sterile | sterile |

TABLE 13

Endotoxin

| Time-point | T69 | T70 | T72 | T76 | T77 | T78 | Upper limit | Unit |
|---|---|---|---|---|---|---|---|---|
| 0 M | 0.17 | 0.10 | 0.08 | <0.03 | <0.03 | <0.03 | 20 | IU/100000 IU |
| 12 M | 0.06 | 0.07 | 0.06 | <0.03 | <0.03 | <0.03 | | |
| 24 M | 0.04 | 0.05 | 0.04 | <0.03 | <0.03 | <0.03 | | |
| 36 M | <0.06 | <0.06 | <0.05 | <0.03 | <0.03 | <0.03 | | |
| 48 M | <0.06 | 0.03 | 0.03 | <0.03 | <0.03 | <0.03 | | |
| 60 M | <0.03 | 0.03 | <0.05 | | | | | |

The method proves that the rHuEPO product, being stored at 2-8° C., is stable and suitable for human use even after 60 months of storage. In comparison to current products, that have an approved shelf-life of about 2 years, this results in a significant improvement in the stability of the resultant product.

The invention now being fully described it will be apparent to one of ordinary skill in the art that many changes and modifications can be made thereto without departing from the spirit or scope of the appended claims.

What is claimed is:

1. A method for purifying recombinant human erythropoietin alpha comprising:
   a. Subjecting unpurified erythropoietin alpha manufactured from a Chinese hamster ovary cell (CHO), a baby hamster kidney fibroblasts cell (BHK), or a HeLa cell, to anion exchange chromatography; said anion exchange chromatography step comprising a wash buffer containing Urea; and collecting the resultant eluent from said anion exchange chromatography, and
   b. further subjecting the resultant eluent from step a to an ammonium sulfate precipitation step having a concentration of ammonium sulfate between 3.6 M and 2.0M; filtering a precipitate from the ammonium sulfate precipitation step and collecting the resulting filtrate, and c. further subjecting the resultant filtrate from step b to a hydrophobic interaction chromatography step and collecting the resultant eluent, and
d. further subjecting the resultant eluent from step c to an acetonitrile addition and collecting said diluent, and
e. further subjecting the resultant diluent from step d to a reversed phase chromatography step and collecting the resultant eluent, and
f. further subjecting the resultant eluent from step e to a second anion exchange chromatography step and collecting the resultant eluent, and
g. further subjecting the resultant eluent from step f to a gel filtration for buffer exchange and collecting the resulting eluent, and
h. further subjecting the resultant eluent from step g to nanofiltration for virus removal.

2. The method of claim 1 wherein the method results in a recombinant human erythropoietin alpha product that is substantially free of non-O-glycosylated recombinant human erythropoietin alpha isoforms.

3. The method of claim 1 wherein the wash buffer of step a comprises a urea concentration of 6M.

4. The method of claim 1 wherein the wash buffer of step a comprises a urea concentration of less than 3M.

5. The method of claim 1 wherein the wash buffer of step a comprises a urea concentration of less than 1M.

6. The method of claim 1 wherein the wash buffer of step a comprises a urea concentration of less than 0.1M.

7. The method of claim 1 further comprising the step of filling said product of step h into a Type 1 glass container for storage of the purified recombinant human erythropoietin alpha product.

8. The method of claim 1, wherein a suitable fraction of the resultant eluent is collected in step e.

9. The process of claim 1, wherein the ammonium sulfate precipitation step is filtered and the resultant filtrate from step b, is subjected to hydrophobic interaction chromatography of step c, without dilution of the filtrate from step b.

10. A multi-step process for the production of a stable recombinant human erythropoietin alpha product that is substantially free of non-O-glycosylated recombinant human erythropoietin alpha isoforms comprising the following steps:
    a. Subjecting a sample comprising recombinant human erythropoietin alpha and impurities to anion exchange chromatography, utilizing wash buffer having a urea concentration of about 6M, and collecting the elute from said chromatography step, and
    b. further subjecting the resultant eluent from step a to an ammonium sulfate precipitation step with a concentration of ammonium sulfate between 3.6 M and 2.0M, filtering the precipitate, and collecting the resulting filtrate, and
    c. further subjecting the undiluted resultant filtrate from step b to a hydrophobic interaction chromatography step and collecting the eluent, and
    d. further subjecting the resultant eluent from step c to an acetonitrile addition and collecting said diluent, and
    e. further subjecting the resultant diluent from step d to a reversed phase chromatography step and collecting the eluent, and
    f. further subjecting the resultant eluent from step e to a second anion exchange chromatography step and collecting the eluent, and
    g. further subjecting the resultant eluent from step f to a gel filtration for buffer exchange and collecting the eluent, and
    h. further subjecting the resultant eluent from step g to nanofiltration for virus removal.

11. The process of claim 10, wherein a suitable fraction of the resultant eluent is collected in step e.

* * * * *